United States Patent
O'Brien et al.

(10) Patent No.: US 6,575,932 B1
(45) Date of Patent: Jun. 10, 2003

(54) ADJUSTABLE MULTI-BALLOON LOCAL DELIVERY DEVICE

(75) Inventors: Edward O'Brien, Ottawa (CA); Marino Labinaz, Manotick (CA)

(73) Assignee: Ottawa Heart Institute, Ottawa (CA)

( * ) Notice: Subject to any disclaimer, the term of this patent is extended or adjusted under 35 U.S.C. 154(b) by 0 days.

(21) Appl. No.: 09/728,600

(22) Filed: Dec. 1, 2000

Related U.S. Application Data
(60) Provisional application No. 60/168,569, filed on Dec. 2, 1999.

(51) Int. Cl.[7] .............................................. A61M 25/00
(52) U.S. Cl. ............................. 604/101.01; 604/103.01
(58) Field of Search .............................. 604/101.01, 53, 604/104, 102, 96, 19, 22, 27, 43, 35, 49, 101.03; 126/4; 606/49, 192

(56) References Cited

U.S. PATENT DOCUMENTS

| | | | |
|---|---|---|---|
| 4,655,746 A | * 4/1987 | Daniels et al. ................ 604/53 |
| 4,824,436 A | 4/1989 | Wolinsky ..................... 604/53 |
| 5,090,960 A | 2/1992 | Don Michael .............. 604/101 |
| 5,176,638 A | 1/1993 | Don Michael .............. 604/101 |
| 5,342,306 A | 8/1994 | Don Michael .............. 604/101 |
| 5,349,942 A | * 9/1994 | Heimberger .................... 126/4 |
| 5,380,284 A | 1/1995 | Don Michael .............. 601/101 |
| 5,460,610 A | 10/1995 | Don Michael .............. 604/101 |
| 5,462,529 A | * 10/1995 | Simpson et al. ............ 604/101 |
| 5,662,609 A | 9/1997 | Slepian ...................... 604/101 |
| 5,704,908 A | 1/1998 | Hofmann et al. .............. 604/21 |
| 5,817,113 A | 10/1998 | Gifford, III et al. ........ 606/153 |
| 5,820,595 A | * 10/1998 | Parodi ........................ 604/101 |
| 5,827,227 A | * 10/1998 | DeLago ...................... 604/104 |
| 5,855,546 A | 1/1999 | Hastings et al. ............... 600/3 |
| 5,919,163 A | 7/1999 | Glickman ................... 604/101 |

* cited by examiner

*Primary Examiner*—Henry Bennett
*Assistant Examiner*—Sabrina Dagostino
(74) *Attorney, Agent, or Firm*—Heslin Rothenberg Farley & Mesiti P.C.

(57) ABSTRACT

The present invention pertains to a local delivery device comprising a distal catheter unit and a proximal catheter unit which may be positioned by sliding over the distal catheter unit. Both the distal and the proximal catheter units have separate inflatable occluding balloons. The slidable positioning of the catheter units in relation to each other provides for variable inter-balloon distances, which in turn provides for a variably sized occlusion region in a hollow tubular organ, for example a vessel. Dispersed on the catheter shaft between the two occluding balloons are multiple infusion ports through which therapeutic agents may be delivered to an occluded region of a hollow tubular organ. The local delivery device may further comprise a quantifying device for determining the distance between the two occluding balloons. Therefore, precise adjustment of the inter-balloon distance permits controlled delivery of therapeutics to a discreet length of the hollow tubular organ wall.

27 Claims, 3 Drawing Sheets

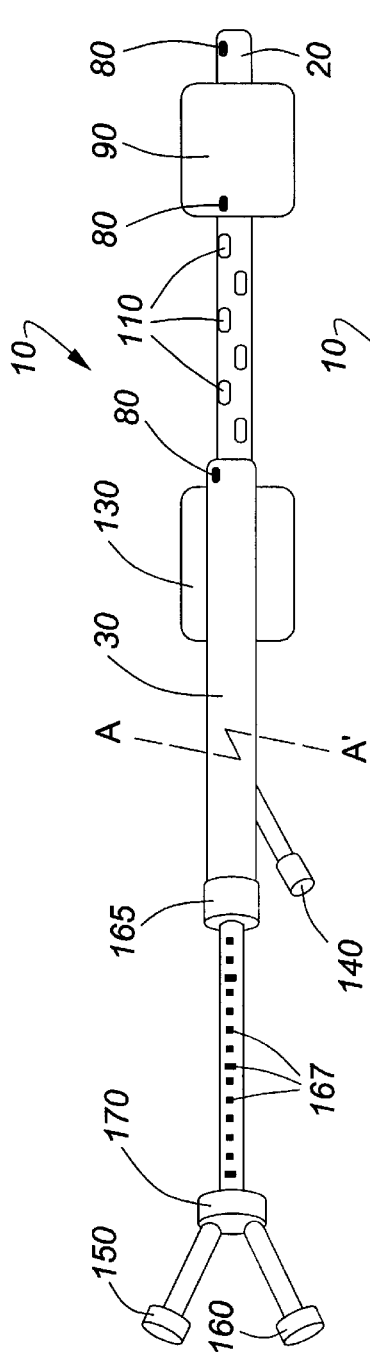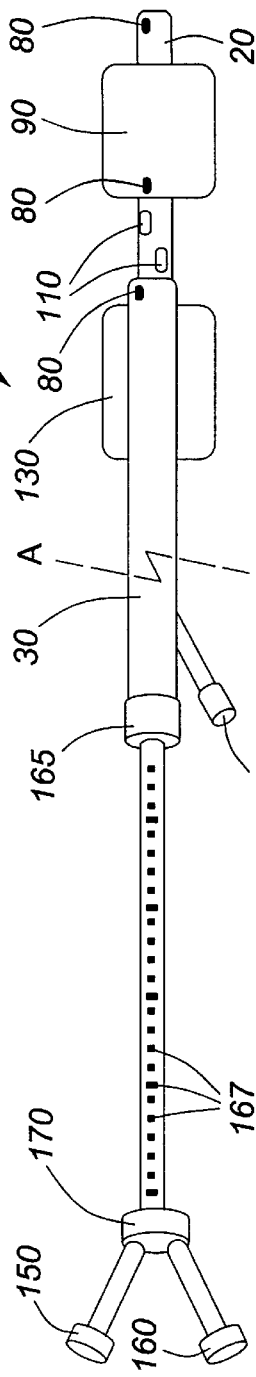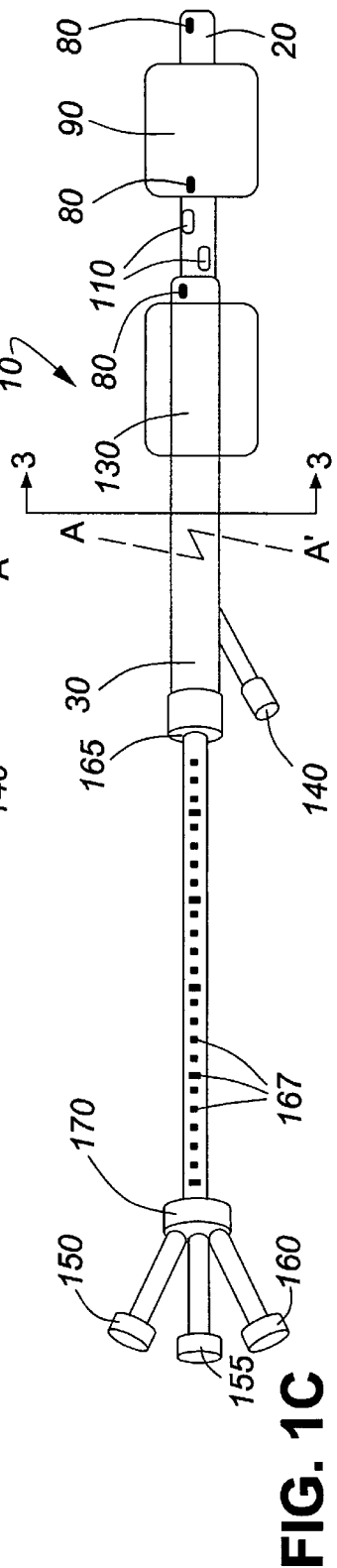

ADJUSTABLE MULTI-BALLOON LOCAL DELIVERY DEVICE

CROSS REFERENCE TO RELATED APPLICATIONS

This application claims the priority of U.S. application Ser. No. 60/168,569, filed Dec. 2, 1999, the entire disclosure of which is incorporated herein by reference.

FIELD OF THE INVENTION

The present invention relates to a local delivery device for the delivery of a therapeutic agent to a hollow tubular organ. More specifically the present invention relates to a multi-balloon catheter with an adjustable inter-balloon distance, adapted for delivery of a therapeutic agent to one or more variable lengths of a hollow organ segment.

BACKGROUND OF THE INVENTION

Vascular and lumenal catheters are widely used in medicine to treat a variety of vascular and lumenal diseases. In some instances, a catheter comprising an inflatable element such as a balloon is used to physically remove deposits on the interior of a tissue lumen. In other instances a catheter is used to deliver a therapeutic agent to a diseased portion of a tissue lumen. There are also catheters which combine inflatable elements and therapeutic agent delivery systems with the aim of treating diseased vessels.

Several recent catheter descriptions pertain to the use of dual-balloon catheters that when inflated define a sealed space suitable for the delivery of a drug or other therapeutic agent. In the catheter designs, the space between the two balloons is fixed. For example, U.S. Pat. No. 5,320,604 to Baxter-International Inc, discloses a single-lumen balloon catheter for embolectomy, dilation, occlusion and infusion of treatment fluids. The catheter shaft comprises a pair of expandable balloons spaced apart on the catheter. Located between the catheters is an infusion section comprising a perforation in fluid communication with the lumen of the catheter. Drugs or other treatment fluids may be delivered via the infusion section to the occluded region of the diseased tissue lumen. Analogous designs are provided for in U.S. Pat. No. 5,460,610 and U.S. Pat. No. 5,380,284. A three balloon catheter is disclosed in U.S. Pat. No. 5,176,638.

Similarly, U.S. Pat. No. 4,824,436 to Wolinsky describes a process for local administration of heparin and other agents to inhibit arterial smooth muscle cell proliferation using a catheter. The catheter contemplated in U.S. Pat. No. 4,824,436 comprises a proximal balloon and a distal balloon separated by a fixed distance. Located on the catheter, in between the two balloons is a perforation which is connected to an infusion lumen in the catheter. Heparin or other agents may be delivered through the catheter lumen to a vascular segment which has been occluded by inflation of both balloons. Also disclosed in the invention is the optional presence of a third balloon located in between the proximal and distal balloons referred to previously. The third balloon may be used to treat plaque deposits in vascular structures. After the middle balloon is deflated the proximal and distal balloons are expanded to create a chamber around the angioplasty site for the delivery therapeutic materials such as heparin. Following delivery of therapeutic material, the balloons are deflated and the catheter is removed. U.S. Pat. No. 5,662,609 relates to a catheter and a technique for treating diseased portions of tissue lumens by the introduction of at least one therapeutic agent at the diseased region. A catheter is positioned in a lumen such that a first and a second expansile member surrounds a diseased portion of tissue. Both expansile members are inflated to occlude the diseased region. A therapeutic agent is introduced into the occluded region of the diseased tissue lumen from a perfusion port located between the two expansile members. The catheter may also have other expansile members located in between, or outside of the first two expansile members. For example, a third expansile member may be provided between the first two expansile members. The inflation of the third member may function as an angioplasty balloon or other disruptive means. The devices disclosed in U.S. Pat. No. 4,824,436 and U.S. Pat. No. 5,662,609 require a plurality of lumens which increases the diameter of the catheter and therefore limits their use to hollow tubular organs of substantial cross section.

In U.S. Pat No. 5,817,113 to Heartport Inc, a drug delivery catheter which has a distal balloon and a proximal balloon separated by a few centimeters distance along the catheter shaft is disclosed. The catheter may have a single inflation lumen which connects to both balloons or separate inflation lumens. The catheter may also be provided with a flushing lumen which connects to a flushing port located on the catheter shaft for flushing of the site with saline to improve visibility of the structure. It is also disclosed that the catheter has a perfusion lumen for blood flow through the catheter. Drugs or other therapeutic molecules may be delivered via a lumen of the catheter to the drug delivery port on the catheter shaft located between the inflated balloons. U.S. Pat. No. 5,090,960, teaches the use of an offset two-catheter, two-balloon system. One catheter comprises a delivery port, and he other catheter a withdrawal port. One eccentric balloon is attached to each of the two catheters, and when inflated, these balloons push each of the catheters against the wall of the vessel. This catheter also provides openings on either side of the balloons, outside the isolated region, for the perfusion of blood through one of the catheters to ensure blood flow when the balloons are inflated.

U.S. Pat. No. 5,855,546 to Sci-Med Life Systems discloses a catheter device capable of simultaneous irradiation of blood vessels, angioplasty and drug infusion. The catheter is equipped with a helical perfusion balloon which when inflated defines a perfusion lumen which facilitates blood flow through the occluded artery portion. The catheter also comprises a lumen with perforations interspersed between the balloon windings to provide a confined volume for delivery of drugs to the vessel wall alone or in combination with radiation therapy.

U.S. Pat. No. 5,704,908 to Genetronics discloses an electroporation catheter for introducing molecules into cells at selected locations within a endoluminal structure. One embodiment comprises a pair of balloons spaced apart at a fixed distance on a guidewire. Each balloon comprises a separate electrode coating which in operation promotes electroporation of drugs or genes trapped or confined to the inter-balloon space into the cells of the endoluminal structure.

The above catheters provide for the delivery of a therapeutic agent to an isolated portion of a vascular segment, thereby permitting the treatment of the vessel lumen with one or a combination of therapeutic modalities, for instance, radiation, drugs, or genetic constructs. However, in all of these devices, the inter-balloon distance is fixed and the length of the vessel lumen which may be perfused with drugs is limited by the distance between the occluding balloons in the catheter structure.

U.S. Pat. No. 5,820,595 discloses an adjustable dual balloon catheter, however, there is no teaching that this catheter may be used as a local delivery device.

U.S. Pat. No. 5,919,163 relates to a dual balloon catheter with openings along the catheter stem located there between. The perforations along the catheter stem function to remove contaminated blood from the body. This catheter is used to isolate a region of interest and withdraw contaminated blood for further processing. The inter-balloon spacing of this catheter is adjustable, however the spacing is determined prior to insertion within the blood vessel. There is no teaching of drug delivery using this dual balloon catheter.

U.S. Pat. No. 5,342,306 discloses an adjustable dual balloon catheter, that comprises one perforation adjacent to a diffusable barrier that permits the supply of an agent within the isolated region between the two balloon portions. The one diffusion port is located at a fixed distance along the catheter, irrespective of the inter-balloon distance. With an increase in inter-balloon distance, the diffusion rate of any supplied agent within the isolated region would be low, requiring long insertion times for adequate diffusion of the medicament within the isolated region. Perfusion ports that direct blood flow through the catheter, and around the balloons, permit the catheter to remain within a physiological passage for prolonged treatment periods. There is also no disclosure of any mechanism providing for precise adjustment or measurement of the inter-balloon distance while the catheter is inserted in situ. An analogous catheter is disclosed in U.S. Pat. No. 4,655,746, comprising a single infusion port located at the rear of the proximal balloon at one end of the isolated region. The inter-balloon distance within this catheter is determined using contrasting material. No mechanism is disclosed for fine adjustment of the inter-balloon distance when in use.

U.S. Pat. No. 5,462,529 discloses a complex dual balloon catheter comprising three overlapping catheter sleeves, a first sleeve associated with the distal balloon, the second attached to a burden loosening member capable of rotating about the first sleeve, and the third attached to a proximal balloon. The space between the second and first catheter sleeves may be used to introduce a fluid of interest within the inter-balloon region (a single port design). The lumen between the second and third catheter may be used for the removal of blood and other components from the blood vessel loosened by the burden loosening member along with the fluid of interest which aids in flushing the isolated region. There is no method or mechanism disclosed for adjusting the inter-balloon distance when the catheter is in use.

To effect radiation and drug delivery to a long vessel segment, either a multitude of catheters must be available with different lengths of inter-balloon distances and infusion ports, or the catheter must be repositioned within the vascular element to treat adjacent lumenal tissue. Similarly, treatment of hollow tubular organs with localized diseased areas using catheters that infuse a therapeutic agent to a larger than required region may also be undesirable. In the case of adjustable catheters, mechanisms providing for accurate and easy adjustment while in use, is needed, as are catheters that comprise infusion port designs permitting ready delivery of a drug to an isolated region, irrespective of the length of the isolated region. Therefore, there is a need within the art for a multi-balloon catheter that provides for an easily adjustable inter-balloon distance in situ, to optimize the isolation of a diseased hollow organ portion, and provides for the delivery of a therapeutic agent to this isolated area.

It is an object of the invention to overcome defects in the prior art.

The above object is met by the combination of features of the main claims. The sub-claims further disclose further advantageous embodiments of the invention.

SUMMARY OF THE INVENTION

The present invention relates to a local delivery device for the delivery of a therapeutic agent to a hollow tubular organ. More specifically the present invention relates to a multi-balloon catheter with an adjustable inter-balloon distance, adapted for delivery of a therapeutic agent to one or more variable lengths of a hollow organ segment.

The present invention relates to a local delivery device for the administration of a liquid of interest comprising:
   i) a distal catheter unit comprising a distal occluding balloon in communication with a distal occluding inflation port, a distal catheter shaft comprising a plurality of infusion ports distributed within the distal catheter shaft and in fluid communication with a liquid of interest delivery port;
   i) a proximal catheter unit, comprising a proximal occluding balloon in communication with a proximal occluding inflation port, and a proximal catheter shaft, the proximal catheter shaft is slidable over the distal catheter shaft; and
   iii) an adjustment mechanism for setting a distance between the distal occluding balloon and the proximal occluding balloon.

The present invention is also directed to a local delivery device as defined above, wherein the adjustment mechanism is selected from the group consisting of a threaded screw adjustment mechanism, a rack and pinion adjustment mechanism, a toothed displacement mechanism, a hydraulic regulated displacement mechanism, a compressed air regulated displacement mechanism, a frictional slide adjustment mechanism, a motor drive adjusted mechanism, and an automatic pull back adjustment mechanism, the adjustment mechanism interacting with either the distal catheter shaft, the proximal catheter shaft, or both the distal and proximal catheter shafts. Actuating the adjustment mechanism causes the proximal catheter shaft or the distal catheter shaft to move relative to each other, and thereby adjust the number of exposed infusion ports.

The present invention also pertains to the local delivery device as defined above, further comprising a quantifying device for determining the distance between the distal occluding balloon and the proximal occluding balloon.

The present invention also pertains to the local delivery device as defined above wherein a valve element, comprising an "O" ring hemostatic valve, is associated with the adjustment mechanism. The adjustment mechanism may also be a threaded screw adjustment mechanism, or a frictional slide adjustment mechanism.

The present invention also embraces the local delivery device as defined above, wherein the distal catheter unit further comprises a lumen traversing the terminal portion of the distal catheter shaft and capable of receiving a guidewire. It is also contemplated that a lumen traversing the entire length of the distal catheter shaft, may receive a guidewire.

This invention also pertains to the local delivery device as defined above, wherein the proximal catheter shaft comprises within its inner surface a sealing element, the sealing element capable of forming a seal between the proximal catheter shaft and the distal catheter shaft thereby sealing the infusion ports residing within the proximal catheter shaft.

This invention also considers a method of administering a therapeutic agent to a hollow tubular organ comprising:

i) inserting the local delivery device defined above within the hollow tubular organ;

ii) inflating one or both of the distal and proximal occluding balloons;

iii) inflating the other of the distal or proximal occluding balloons to produce an occluded space;

iv) evacuating or flushing the occluded space; and v) introducing the therapeutic agent into the occluded space.

It is also contemplated that after steps i) or ii), there follows a step of actuating the adjustment mechanism to alter the distance between the proximal and distal occluding balloons.

The present invention also relates to the above method, wherein the step of introducing, step iv), involves introducing the therapeutic agent under pressure, or via electroporation.

The present invention includes the above method, wherein the therapeutic agent is selected from the group consisting of a drug, a nucleotide sequence encoding a protein of interest, and a construct comprising a nucleotide sequence encoding a protein of interest. The therapeutic agent may be administered within a liposome, or as an emulsion, microemulsion or along with a cationic lipid. Furthermore, the nucleotide sequence or the construct comprising a nucleotide sequence may be administered within a bacterial, or viral vector.

The present invention is also directed to the method as defined above wherein the therapeutic agent is a photoactivated therapeutic agent, and the local delivery device further comprises one or more fibre optic strands directing light from a light source to a treatment site, thereby activating the photoactivated compound.

The present invention also provides for the method as defined above wherein the therapeutic agent is an antithrombic therapeutic agent or a radio-sensitized therapeutic agent, and the local delivery device further comprises a radioactive source.

The present invention also embraces a method of measuring an inter-balloon distance in a local delivery device when the local delivery device is inserted within a subject, comprising measuring the inter-balloon distance using a graduated scale.

The local delivery device of the present invention permits a variety of inter-catheter balloon distances to be established even while the local delivery device is inserted within a hollow tubular organ. By regulating the distance between a proximal and distal catheter balloon, the administration of a therapeutic agent or liquid of interest can be targeted to a specific site and minimise the exposure of non diseased tissue to the therapeutic agent. Furthermore, by providing a plurality of ports within the catheter, the fluid of interest can be readily administered to the treatment site. In doing so, shorter delivery times, and more uniform delivery may be achieved. As a result of the efficient delivery of a liquid of interest to a treatment site, ports to permit distal perfusion of the hollow organ may not be required for some applications, therefore, the overall diameter of the catheter can be reduced. This simplified design permits use of the local delivery device of the present invention within smaller hollow tube organs than can be achieved using current catheter designs.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 1 is an embodiment of an aspect of a local delivery device of the present invention. For clarity, the entire local delivery device has not been shown nor is the figure drawn to scale. The dashed line A–A' represents a break in the continuum of the catheter. FIG. 1*a* shows the catheter in an extended configuration. FIG. 1*b* shows the catheter with a reduced inter-balloon distance.

FIG. 3 shows several varied embodiments of the local delivery device shown in FIG. 1.

DESCRIPTION OF PREFERRED EMBODIMENT

Figure 2:
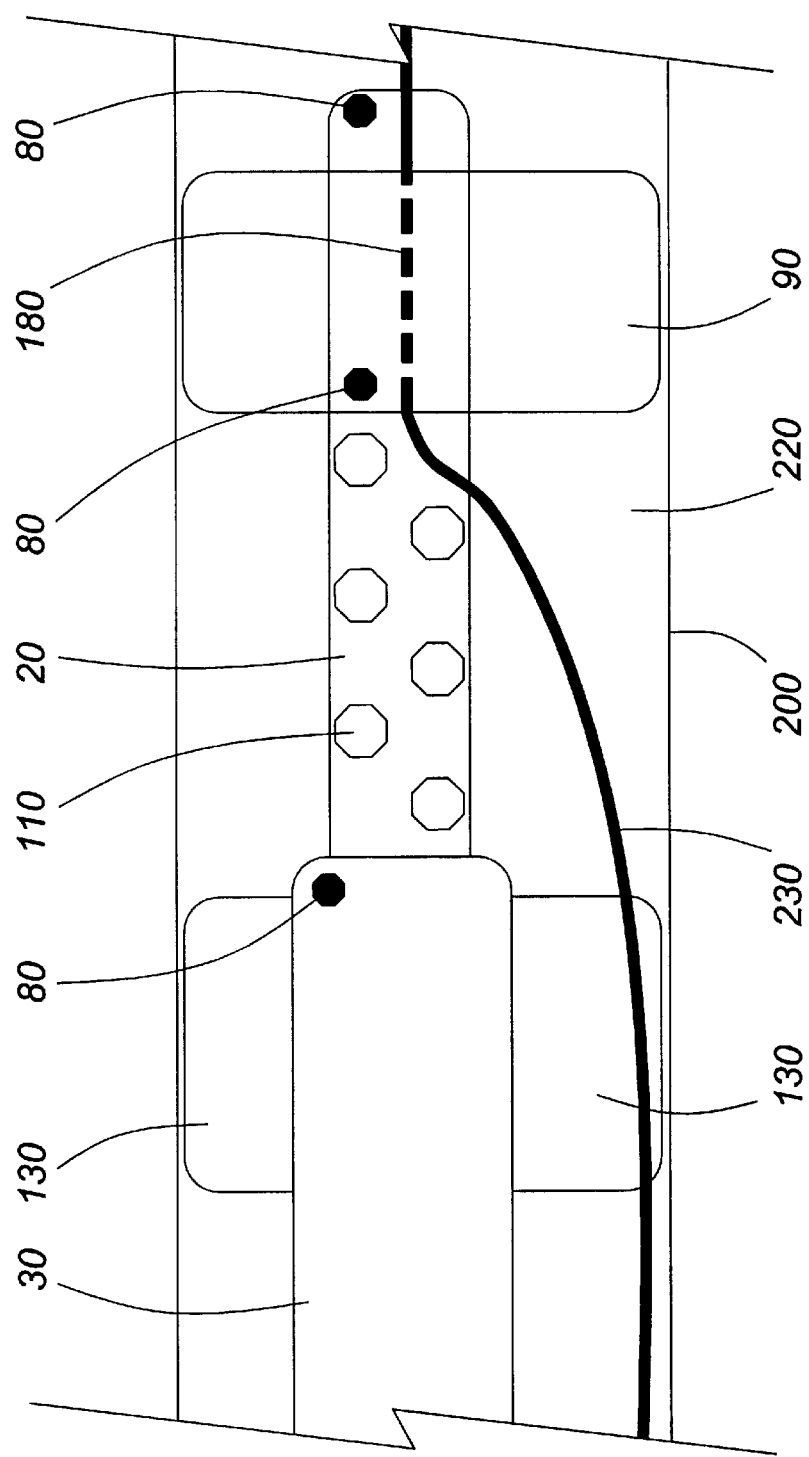
FIG. 2 is an embodiment of an aspect of a local delivery device of the present invention which has been inserted into a vessel. For clarity, the entire local delivery device has not been shown nor is the figure drawn to scale. The dashed line A–A' represents a break in the continuum of the catheter.

The present invention relates to a local delivery device for the delivery of a therapeutic agent to a hollow tubular organ. More specifically the present invention relates to a multi-balloon catheter with an adjustable inter-balloon distance, adapted for delivery of a therapeutic agent to one or more variable lengths of a hollow organ segment.

The following description is of a preferred embodiment by way of example only and without limitation to the combination of features necessary for carrying the invention into effect.

By "hollow tube organ", it is meant any lumen within an animal that can be treated using a local delivery device of the present invention. Examples of a hollow tube organ include, but are not limited to, blood vessels, including arteries and veins, bronchial passages, the gastrointestinal tract, including the esophagus, genital/urinary tract, urethra and ureter.

By "agent of interest" it is meant a compound, fluid, or liquid of interest, or an agent that may participate in the activation of a compound, fluid or liquid of interest that has been administered to a desired site. For example, an agent of interest may include, but is not limited to a light source capable of photoactivating or sensitizing a photoactivated or photosensitized compound. An agent of interest may also include, but is not limited to, a radioactive source, for example located a radioactive wire, that sensitizes or activates a radiation sensitizing agent.

By "fluid of interest", "liquid of interest" or "therapeutic agent" it is meant any fluid, liquid or therapeutic agent that is to be delivered via the catheter, or local delivery device of the present invention, to a region of the hollow tube organ within which the catheter has been positioned. Preferably, the region of administration of the fluid, liquid or therapeutic agent is isolated from the rest of the hollow tube organ by expanding the occluding balloons as described below, and the liquid is administered within the isolated region. Examples, which are not to be considered limiting in any manner, of components of a liquid, fluid or therapeutic agent that may be administered using the catheter of the present invention include:

- drugs for example, antithrombic and antiproliferative agents, for example, but not limited to heparin, cilazapril, enoxaparin, glucocorticoids, for example corticosteroids, photoactivated or photosensitized, and radio-sensitized (for example but not limited to nitroimidazole hypoxic agents, including pimonidazole) compounds. It is also contemplated that several drugs may be sequentially administered as required, for example, but not limited to an active agent followed by an inactivating agent after a period of time. An example of an activating agent, which is not to be considered limiting in any manner, may be a pharmaceutically active compound, and an inactivating agent, a neutralizing agent;
- proteins, for example, enzymes, including nitrous oxide synthase, or antibodies directed against specific target receptors or proteins. It is also contemplated that several proteins may be sequentially administered as required, for example, but not limited to an active agent followed by an inactivating agent after a period of time. An example of an activating agent, which is not to be considered limiting in any manner, may be a protein, and an inactivating agent a protease;
- nucleic acid sequences, alone or within a suitable delivery vehicle, for example, liposomes, optionally delivered in conjunction with inactivated viral particles, or retroviral or adenoviral vectors. Examples, of nucleic acid sequences include, oligonucleotides, homeobox genes, for example GAX (growth arrest homeobox), DNA encoding thymidine kinase delivered in combination with gancyclovir, nitrous oxide synthase, retinoblastoma gene product, antisense oligonucleotides, for example directed to gene products involved in restenosis or other proliferative processes, nucleic acid sequences for gene therapy, or for regulating cell cycle, for example, cyclin dependant kinase inhibitors;
- biodegradable microparticles and biodegradable polymers impregnated with a drug of interest;
- inert solutions for flushing the region as needed, for example PBS.

It is also contemplated that combinations of components may be administered to a region within a hollow tube organ using the delivery device of the present invention. Other components that may be included within a liquid or fluid of interest are disclosed in but not limited to Brieger et al (1997, Cardiovas. Res. 3 5:405–413; which is incorporated herein by reference), Tahlil et al. (1997, Cardiovasc. Res. 33: 181–187; which is incorporated herein by reference), von der Leyen et al. (1999, Human Gene Therapy 10:2355–2364; which is incorporated herein by reference).

It is also considered that the local delivery device of the present invention may be used to administer one or more therapeutic or other agents of interest including, in addition to a fluid of interest as defined above. A therapeutic, or other, agent of interest may comprise, but is not limited to, a light, radioactive, heat, or cooling source Referring now to FIGS. 1(a), (b), and (c), according to the present invention there is provided a local delivery device (10) comprising at least one catheter unit, either a distal catheter unit (20) or a proximal catheter unit (30), a combination thereof. The distal catheter unit (20) is adapted to traverse within the proximal catheter unit (30). Furthermore, it is to be understood that other medical devices may be adapted to either slide within the proximal catheter unit, or slide over the distal catheter as required. Such other medical devices include catheters or wires comprising ultrasonic devices, lasers, fibre optics, electroporation, or radioactive isotopes, for example, but not limited to devices disclosed in U.S. Pat. No. 4,905,689, U.S. Pat. No. 4,878,492, U.S. Pat. No. 5,196,004, U.S. Pat. No. 5,250,045, U.S. Pat. No. 4,848,336, U.S. Pat. No. 4,905,689, U.S. Pat. No. 5,855,546, U.S. Pat. No. 5,704,908 (all of which are incorporated herein by reference). In this regard the catheter of the present invention may be used to deliver a therapeutic agent as the liquid of interest to a target treatment site and an additional component of the catheter may act as an agent of interest, and be used to activate the therapeutic agent and ensure activity within a localized area. For example, one or more photoactivated therapeutic agents may be administered, to a target region (see for example, but not limited to U.S. Pat. No. 5,238,940, U.S. Pat. No. 6,103,751, U.S. Pat. No. 5,506,255, all of which are incorporated herein by reference), or one or more radio-sensitized therapeutic agents may be administered, for example, but not limited to nitroimidazole hypotoxic agents, such as pimonidazole, using the catheter of the present invention. Following delivery of the therapeutic agent, a photoactivated agent is activated using light of an appropriate wave length provided via an optic fibre inserted within the same delivery catheter. The optical fibre is positioned to emit the light within the isolated region thereby activating the photoactivated therapeutic agent at the treatment site. Similarly, a radio-sensitized agent may be activated by introducing an appropriate radiation source (e.g. WO 99/15234, U.S. Pat. No. 5,575,749, U.S. Pat. No. 5,498,227, which are incorporated herein by reference) within the same delivery catheter. Other synergistic applications involve the administration of a liquid of interest, for example a drug, along with exposure of the treatment site to a radioactive source. In this embodiment, a drug, for example, but not limited to an antithrombic agent may be administered as a liquid of interest, while at the same time, the treatment site can be exposed to ionizing radiation, for example, P-32, C-14, S-35, Y-90, Pd-103, Co-55, Co-57, Co-60, Ag-110, Ag-111, Ag-112, Ag-113, Au-199, Cu-64, Re-186, Re-188, Ir-192, Ir-194, Mo-99, Ni-63, In-111 and Tc-99m. The source for ionizing radiation maybe provided within a wire, for example, as a radioactive seed, for example, but not limited to WO 99/15234, U.S. Pat. No. 5,575,749 (which are incorporated herein by reference), or portion of the wire may be made radioactive, for example but not limited to U.S. Pat. No. 5,498,227 (which is incorporated herein by reference), and this wire is introduced into the catheter to the treatment site.

The distal catheter unit (20) comprises one or more radiopaque markers (80), a distal catheter occluding balloon (90), a plurality of infusion ports distributed along the shaft of the distal catheter (110), a distal occluding balloon inflation port (150), an optional guide wire delivery port (155, FIG. 1(c)), a therapeutic agent, or liquid of interest, delivery port (160), an optional scale (167) or other quantifying device, a port connection means (170) and at least one lumen (180, FIG. 2).

The scale or other quantifying device used to determine the inter-balloon distance, may comprise any mechanism that may be used to readily determine the inter-balloon distance from outside the body. For example, which is not to be considered limiting in any manner, the quantifying device may comprise a motor drive mechanism that feeds or withdraws the distal catheter at a regular rate relative to the proximal catheter, for example, but not limited to an automatic pull back (Cardiovascular Imaging Systems). Furthermore, the scale or other quantifying device may comprise a screw thread or similar mechanism that may be used to determine the inter-balloon distance.

The radiopaque markers (80) may be used to provide a means for determining the position and location of specific elements on the distal catheter in a hollow tubular organ during insertion and during therapy or other treatment. Furthermore, equidistant, radiopaque markers may be added to the shaft of the distal catheter in order to provide a scale along the distal catheter shaft amongst the perfusion ports so that the inter-balloon distance may be confirmed by imaging the radiopaque scale.

The distal catheter occluding balloon (90) may be any suitable dimension for use within a desired hollow tubular organ. For example, which is not to be considered limiting in any manner, within an artery, the balloon may be of about 5 mm in length and of about 3.0, 3.5 or 4.0 mm in diameter. Other balloon lengths and diameters may be required depending upon requirements of a selected hollow organ. Furthermore, other balloon sizes are also contemplated, specifically but not meant to be limiting, to compensate for the variation in the diameters between the distal catheter unit (20) and the proximal catheter unit (30).

Figure 3A:
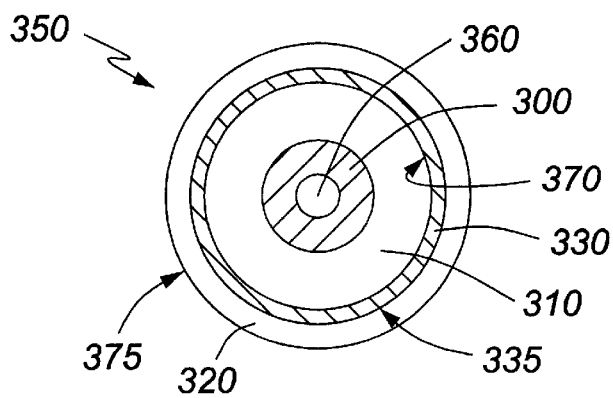
FIG. 3*a* shows one possible cross-sectional view along line 3—3 as shown in FIG. 1, displaying a number of concentric lumens which may be employed to inflate balloons or deliver therapeutic agents.

The distal catheter occluding balloon (90) is inflated from a distal occluding balloon inflation port (150) which connects via a distal catheter occluding balloon lumen (300, FIG. 3(a), (b) or (c)) that travels through the distal catheter unit (20). Therapeutic agents, or liquids of interest, may be administered via the therapeutic agent (liquid of interest) delivery port (160), through the therapeutic agent (liquids of interest) infusion lumen (310, FIG. 3) which also traverses the distal catheter unit (20), to the infusion ports (110) where the one or more liquids of interest (therapeutic agents) are released into a hollow tubular organ requiring treatment. The port connector means (170) connects both the distal balloon inflation port (150) and the therapeutic agent (liquid of interest) delivery port (160) to the proper lumens of the distal catheter unit (20). A scale (167) may be used to accurately determine the length of the distance between the distal occluding catheter balloon (90) and the proximal occluding catheter balloon (130). As can be seen with reference to FIG. 1(a), (b) or (c), this scale permits determination of the inter-balloon distance from outside the body. It is also contemplated that equidistant, radiopaque markers may be added to the shaft of the distal catheter amongst the perfusion ports, in order to provide a scale along the distal catheter shaft to provide a separate or an additional method for in situ determination of the inter-balloon distance.

The main shaft of the distal catheter comprises a series of perforations or ports (110) for local delivery of a liquid of interest. The ports are spaced at regular intervals, for example, but not limited to, 2 mm intervals, and they are oriented to provide equal delivery to all regions of the hollow tubular organ located between the distal and proximal balloons. A delivery port (160) connects with this portion of the catheter. The distal end of the delivery port ends in a cul de sac proximal to the distal balloon. By having the ports (110) located along the distal catheter shaft (20), and not the annular (distal) end of catheter 30, the fluid of interest is delivered at right angles to the isolated hollow tube organ resulting in an efficient delivery of the delivered fluid. By having the ports positioned perpendicular to the catheter, an active delivery of the fluid of interest to the surface of the isolated region within the hollow tube organ is achieved. Furthermore, if penetration of the therapeutic agent within the tissue of the treatment site is required, then the opening size of the ports may be reduced to increase the fluid pressure. Similarly, the fluid of interest may be administered under a greater pressure. However, it is to be understood that if required, the fluid of interest may be delivered from ports 110 in a slow manner as the situation requires, for example, but not limited to, diffusion. By having the ports positioned along the length of the catheter shaft 20, between occluding balloons 90 and 130, a rapid, uniform delivery of the liquid of interest is achieved. This rapid, uniform delivery reduces the occlusion time during which balloons of the catheter remain inflated within the hollow tube organ. If the hollow tube organ is an artery or blood vessel, delivery of a fluid of interest may take place without requiring perfusion of blood through the catheter through optional perfusion ports. This simplifies the catheter design, and reduces the overall diameter of the catheter. Catheters of reduced diameter may be used for the treatment of hollow tube organs of narrow diameter that are normally not accessible to bulkier catheters of the prior art.

It is also contemplated that an agent of interest, including but not limited to a light, radioactive, heat or cooling source may be inserted within the catheter, and the ports (110) reduce the attenuation of the agent of interest, thereby enhancing the activity of the agent interest. For example, which is not to be considered limiting, if the agent of interest is a light source, and the therapeutic agent is a photo-activated compound the ports may be elongated to provide an elongate window through which the light may interact with the therapeutic agent. Similar elongated windows may be used to enhance the synergistic action of a radioactive source and a radio-sensitized therapeutic agent.

The ports (110) may also be used to remove the administered liquid of interest, or native fluid, from within the hollow tube organ as required. If the catheter of the present invention has been used to administer a fluid of interest to an isolated region, by determining the precise inter-balloon distance, the volume of administered liquid of interest can be determined and the same volume of fluid may be removed. However, it is to be understood that by partially deflating either the one proximal or distal balloon, as the situation requires, regular fluid flow within the hollow tube organ can be used to purge the treatment site, and the native fluid (for example blood) or the native fluid along with the infused liquid, may be removed through the catheter using ports 110.

The proximal catheter unit (30) comprises one or more radiopaque markers (80), a proximal catheter occluding balloon (130), a proximal occluding balloon inflation port (140), a valve element (165) and a seal member (330; FIGS. 3a,b). The radiopaque marker (80) of the proximal catheter unit provides a similar function as the radiopaque marker (80) of the distal catheter unit (20), namely a means for determining the position and location of different parts of the local delivery device in a hollow tubular organ during insertion of the delivery device and during therapy.

The proximal catheter occluding balloon (130) is preferably of the same dimensions as the distal catheter occluding balloon (90), however, catheter units comprising different sized occluding balloons may also be used as required. The proximal occluding balloon (130) is inflated from the proximal occluding balloon inflation port (140) via a proximal catheter occluding balloon lumen (320) which traverses the interior of the proximal catheter (30).

The proximal catheter occluding balloon (130) may be inflated within an endoluminal structure, or hollow tube organ, to occlude a portion of a hollow organ lumen. The distance between the proximal catheter occluding balloon and the distal catheter occluding balloon may be adjusted by way of a valve element (165) prior to inflating either the proximal, distal, or both the proximal and distal occluding balloons as required.

The valve element (165) may comprise, for example but not to be considered limiting in any manner, an "O" ring hemostatic valve and an adjustment mechanism. The adjustment mechanism permits controlled movement of the proximal catheter unit, along, and in relation to, the distal catheter unit. The hemostatic valve, when released (in an open, unlocked position) permits the distance between the proximal and distal catheter units to be adjusted using an adjustment mechanism. The adjustment mechanism may comprise a screw-threaded, rack and pinion, toothed, hydraulic or compressed air regulated displacement, or other slidable, frictional engagement means to establish the desired relative positions of the distal and proximal catheter units, for example but not limited to a motor drive mechanism that feeds or withdraws the distal catheter at a regular rate relative to the proximal catheter, for example, but not limited to an automatic pull back (Cardiovascular Imaging Systems). The adjustment mechanism may be located within valve element 165, or be positioned elsewhere, for example, adjacent the valve element, providing that an accurate determination of the relative positions between the proximal (30) and distal (20) catheters can be obtained using the adjustment mechanism. As one of skill in the art would appreciate, any suitable adjustment mechanism may be employed to set the relative positions between the two catheters. In an unlocked position, the proximal catheter unit (30) may be slidably positioned, for example, by a micrometer adjustment mechanism in relation to the distal catheter unit (20) to allow for variable inter-balloon distances. An optional scale (167) may be disposed on the distal catheter unit (20) outside of the body, and may be used to indicate the distance between the distal occluding balloon (90), and the proximal occluding balloon (130) and thus may indicate the size of the occluded hollow tubular segment when both occluding balloons are inflated within a hollow tubular organ in situ. Furthermore, equidistant, radiopaque markers may be added to the shaft of the distal catheter amongst the perfusion ports, in order to provide a scale along the distal catheter shaft permitting a separate or additional method for in situ determination of the inter-balloon distance.

The proximal catheter unit may also comprise a seal member (330, FIG. 3) intimately associated with the inner shaft of the proximal catheter unit. The seal member (330) inhibits leakage of therapeutic agents or liquids of interest, from covered infusion ports (110) when the proximal catheter unit is slidably positioned over the infusion ports (110) in the distal catheter unit (20). For example, which is not to be considered limiting, the seal member may comprise an elongate seal that is sized so that it covers one or more of the infusion ports residing within the proximal portion of the catheter when the local delivery device is not fully extended (i.e. the proximal and distal catheters are not fully extended relative to each other). In this embodiment, the delivery of a therapeutic agent or liquid agent of interest would be limited to the unsealed-infusion ports residing between the proximal and distal balloons, and no pretreatment of the catheter is required. However, alternative seals assemblies may also be employed that restrict the flow of liquids of interest from the ports of the distal catheter back within the lumen between the distal and proximal catheter. For example, an 'O' ring type seal may be positioned between the two catheters, and proximal to ports 110, when the distal catheter is in its most retracted position. Such a seal would permit easy relative movement between the catheters, but restrict flow of the liquid of interest to the site requiring treatment. In this latter embodiment, the catheter may be pre-primed with saline, through the delivery port (160) prior to introducing a therapeutic agent or liquid of interest.

The following description outlines one of many possible uses of the local delivery device of the present invention, and this description is not to be considered limiting in any manner. In use, a standard interventional guidewire (230) may be inserted in the coronary artery using a standard interventional guiding catheter as is typically used within the art to access the coronary artery. Interventional wires of any suitable diameter may be used for example, but not limited to 0.014". The local delivery device is inserted in closed position, that is the proximal and distal balloons are adjacent to each other and locked via valve element (165). With the local delivery device in the closed position (i.e., both balloons locked in apposition via a proximal "O" ring hemostatic valve (165)) the local delivery device is advanced over the guidewire (230) and threaded into the artery. The guidewire may be threaded through a lumen of the local delivery device through 155 (FIG. 1(C)) that traverses the entire length of the local delivery device (an over the wire system), or the guidewire may be threaded through a lumen (180, FIG. 2) comprising a portion of the local delivery device as with a monorail system, for example, U.S. Pat. No. 5,290,247; U.S. Pat. No. 5,378,236; U.S. Pat. No. 5,836,306 (which are incorporated herein by reference). In this latter case, the monorail portion of the local delivery device is inserted over the guidewire, threaded into the artery, and under fluoroscopic guidance, and positioned at the appropriate site for delivery. The distal radiopaque marker is used to position the catheter tip.

Once in place, the distal (90), proximal (130), or both the distal and proximal catheter occluding balloons may be inflated as required, depending upon the clinical situation, to secure the catheter in position. To do this, the "O" ring hemostatic valve (165) is loosened, and the proximal catheter (30) is withdrawn over the distal catheter (20) in order to expose the desired length of therapeutic delivery ports (110). However, it is to be understood that the adjustment of the inter-balloon distance may be made prior to inflating either of the occluding balloons. For example in situations where a minimal lumen occlusion time is desired, the inter-balloon distance may be set prior to inflating either the proximal or distal occluding balloons, and both the proximal and distal occluding balloons inflated simultaneously. Otherwise, the other of the proximal or distal occluding balloon is inflated and the "O" ring hemostatic valve (165) is closed in order to secure the catheter in the artery and lock the position of the two occluding balloons. Local delivery of a therapeutic agent or liquid of interest may then begin via the therapeutic agent (liquid of interest) delivery port (110).

Upon placement of the local delivery device within a hollow tubular 10 organ, a portion of the proximal catheter unit (60) comprising a valve element (165), and proximal catheter occluding balloon inflation port (140), as well as a portion of the distal catheter unit (20) comprising a distal occluding balloon inflation port (150), therapeutic agent delivery port (160), port connector means (170) and scale (167) are located on the exterior of a patient or subject. The proximal end of the device that remains outside the patient's body and visible to the operator consists of an adjustable apparatus for specifying the exact length of hollow tubular organ for local delivery. The proximal catheter can be withdrawn over the main shaft of the distal infusion catheter, and equally spaced markers, other quantifying device, or adjustment mechanism may be used indicate the length of hollow tubular organ that is exposed to the infusion ports. Similarly, the distal catheter may be extended within the shaft of the proximal catheter, again using the adjustment mechanism, other quantifying device, or markers to determine the relative distance between the two catheters. Following a period of delivery of the liquid of interest, the balloons may be deflated, and the catheter repositioned for further treatment, or removed, as required.

The distal catheter occluding balloon (90) may be inflated with any suitable media, for example, which is not to be considered limiting in any manner, saline or a radiopaque dye. Following insertion of the local delivery device the distance between the proximal and distal catheters may be adapted to any length as required. For example, FIG. 1(a) displays the proximal catheter unit (30) slidably positioned over the distal catheter unit (30) such that the distance between the distal and proximal occluding balloons is relatively large, while FIG. 1(b) displays the proximal catheter unit (30) slidably positioned over the distal catheter unit (20) such that the distance between the distal and proximal occluding balloons is relatively small.

If the local delivery device comprises an elongate seal (330) or other seal that is capable of sealing infusion ports residing within the space delimited by the proximal catheter, for example, when the local delivery device is not fully extended, then a fluid of interest or therapeutic agent may be administered following positioning of the delivery device. In the case where the seal member (330) is not an elongate seal, for example an "O" ring, then the volume residing between the distal and proximal catheters (i.e. between the outer surface of the distal catheter (370) and the inner surface of the proximal caterer (335) referred to as "dead volume") may need to be pre-primed with a suitable liquid, for example saline, prior to introduction of a therapeutic agent. There are many ways in which the dead volume may be pre-primed. For example, which is not to be considered limiting, when the distal and proximal catheters are in a retracted position, the therapeutic agent delivery port (160) is used to administer saline to pre-prime the dead volume. Saline is introduced via port 160, and air is permitted to escape through the open hemostatic valve (165). When saline is observed to exit valve 165, then the dead volume is pre-primed. The catheters may then be positioned as required in situ, and a liquid of interest administered as outlined above. It is also possible to first position the local delivery device of the present invention in situ, and then purge or pre-prime the dead space with saline. Once saline exits the hemostatic valve (160), the valve is closed and therapeutic agent administered as required. In this case, during the pre-priming stage, saline is also flushed through the infusion ports (110) positioned between the proximal and distal balloons.

An expanded view of a diseased hollow tubular organ (200) showing a portion of the local delivery device in which the distal catheter occluding balloon (90) and the proximal catheter occluding balloon (130) have been inflated, is shown in FIG. 2. For clarity, only a portion of the local delivery device is shown. Interspersed on the distal catheter unit (20) between the distal catheter occluding balloon (90) and the proximal catheter occluding balloon (130) are infusion ports (110) for the delivery of one or more therapeutic agents, or liquids of interest. The ports are positioned on the catheter to effectively deliver therapeutic agents, or liquids of interest, to all quadrants of an occluded hollow tubular organ (200). The infusion ports (110) begin immediately adjacent to the distal catheter occluding balloon (90) and communicate with a lumen within the distal catheter unit (310, FIGS. 3a, and 3b). The lumen (310) of the distal catheter unit is in fluid communication with the therapeutic agent (liquid of interest) delivery port (160, FIG. 1a,b). Thus, liquids of interest may be delivered from the therapeutic agent delivery port (160), through the lumen (310) of the distal catheter unit via the infusion ports (110) to an occluded hollow tubular organ region (220).

The local delivery device is positioned within a diseased hollow tubular organ (200) with the help of a guidewire (230). Following positioning of the local delivery device at the proper site of a diseased hollow tubular organ (200) the distal catheter occluding balloon (90) may be inflated using any suitable media, for example but not limited to saline or a radiopaque dye. The proximal catheter unit (30) is capable of sliding reversibly over the shaft of the distal catheter unit (20). The relative location of a radiopaque marker (80) located on the proximal catheter unit (30) and adjacent to the proximal catheter occluding balloon (130), compared to the radiopaque markers (80) located on the distal catheter unit (20), provides an indication of the inter-balloon distance and also determines the length of the occluded region of a hollow tubular organ (220). The proximal catheter occluding balloon (130) may be moved toward or away from the distal catheter occluding balloon (90) as required. Similarly, if needed the distal occluding balloon (90) may be deflated and slidably positioned further away from the proximal catheter occluding balloon (130), providing for a variable-length occlusion zone (220) in a hollow tubular organ. Furthermore, the inter-balloon distance maybe established prior to inflating the proximal, distal or both the proximal and distal balloons, depending upon the operators needs. As the distance between the proximal catheter unit (30) and the distal catheter unit (20) increases, infusion ports (110) along the distal catheter unit (20) are uncovered providing for a homogeneous infusion of the occluded hollow tubular organ region (220) by a therapeutic agent.

Figure 3B:
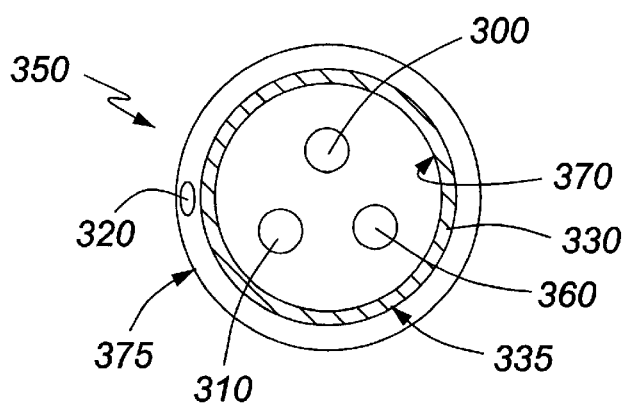
FIG. 3*b* shows another possible cross-sectional view along line 3—3 axis as shown in FIG. 1, displaying an alternate arrangement of lumens within the local delivery device.
Figure 3C:
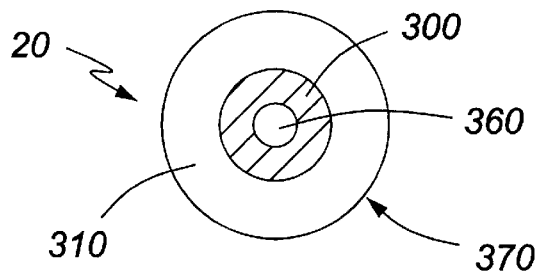
FIG. 3*c* shows a cross section of an embodiment of the distal catheter.
Figure 3D:
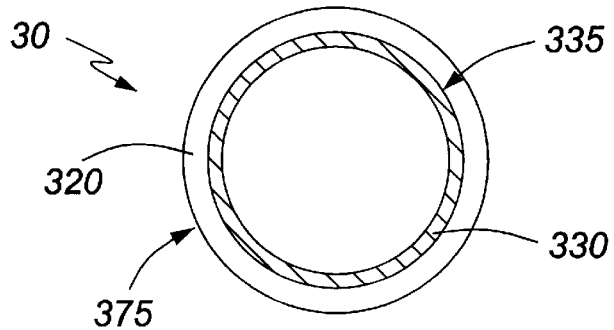
FIG. 3*d* shows a cross section of an embodiment of the proximal catheter.

Referring now to the cross-sectional view of the local delivery device as shown in FIGS. 3(a), 3(c) and 3(d), the local delivery device of the present invention may comprise a multi-lumen structure (350) wherein the lumens are arranged in concentric circles in the plane substantially normal to the long axis of the therapeutic agent drug delivery device (FIG. 3(a)). Shown in FIG. 3(a) is an aspect of the embodiment of the present invention, where the section is taken at 3—3 of FIG. 1. FIG. 3(c) and 3(d) show sections of the distal and proximal catheter, respectively. The local delivery device shown in FIG. 3a, comprises a central guidewire lumen (360), a distal catheter balloon inflation lumen (300), a therapeutic agent delivery lumen (310), the outer surface of the distal catheter unit (370), a seal member (330) attached to the inner surface of the proximal catheter unit (335), a proximal occluding balloon inflation lumen (320) and an outer surface of the proximal catheter unit (375).

Alternatively, the lumens of the local delivery device may be arranged as ducts traversing the length of the local delivery device, the cross section of which is shown in FIG. 3(b). Lumen 360 may be used in combination with a guidewire to direct the catheter to its proper location, for example as indicated in FIG. 2(c), where guidewire 230 enters via guidewire port 155. Alternatively, a guidewire lumen 400 may be formed in a relatively small section of the most distal region of the local delivery device as shown in FIG. 3c to direct the catheter to its proper location. Such a method is generally referred to in the art as a "monorail" system (for example, U.S. Pat. No. 5,290,247; U.S. Pat. No. 5,378,236; U.S. Pat. No. 5,836,306 (which are incorporated herein by reference). In addition to comprising lumens which may accept a guide wire (360, 400), and inflation lumens (300, 320), the local delivery device also contains lumen 310, which is in fluid connection with multiple infusion ports (110, FIGS. 1,2) interspersed on the catheter. Thus, therapeutic substances may be administered through a single lumen of the catheter to an occluded region of a hollow tubular organ via the infusion ports located on the surface of the catheter.

In addition to comprising lumens for inflation of occluding balloons, and delivery of therapeutic agents, the local delivery device may comprise other lumens which traverse part or the entire local delivery device. For example, but not to be considered limiting, the local delivery device may comprise a lumen, for example a perfusion lumen (not shown, but see for example, but not limited to, U.S. Pat. No. 5,342,306, U.S. Pat. No. 4,655,746, which are incorporated by reference) which permits blood to flow past the occluded hollow tubular organ region while the proximal and distal balloon are inflated.

A variety of therapeutic agents may be delivered to the occluded hollow tubular organ region by the local delivery device. These therapeutic agents include drugs or nucleotide sequences, or constructs comprising nucleotide sequences alone, or in combination with a variety of adjuvants. For example, but not to be considered limiting, drugs or nucleotide sequences may be delivered to cells in association with liposomes or cationic lipids, bacterial, and viral vectors which may include adenoviral gene transfer or retroviral gene transfer. Further, therapeutic agents may be formulated and delivered in emulsions or microemulsions, or the therapeutic agent may be conjugated to a macromolecule which is subsequently taken up by a cell. For example, it is well known in the art to conjugate a therapeutic agent to an antibody specific for an antigen localized on the exterior of a cell surface and then administer the therapeutic agent to the cell.

The nucleotide sequences or constructs comprising nucleotide sequences to be introduced into the cells may encode endogenous proteins, or the nucleotide sequences introduced may encode transgenic proteins. Some examples of proteins which may be produced by such nucleotide sequences include but are not limited to vascular endothelial growth factor, and nitric oxide synthase. It is also contemplated that radioactive solutions or slurries, microspheres with covalently attached therapeutic agents, or radioisotopes may be administered via the infusion ports. Nucleotide sequences which transcribe antisense oligonucleotides of genes which encode specific cellular proteins may be used to downregulate the production of a specific protein.

It is also contemplated that the local delivery device may comprise electrodes for electroporation of therapeutic compounds into cells of the occluded region, for example as described in U.S. Pat. No. 5,704,908 (which is incorporated herein by reference). Further, local delivery device of the present invention may comprise a lumen or compartment which may house a radioactive source attached to a guidewire that passes through the catheter, for example as described in U.S. Pat. No. 5,855,546 (which is incorporated herein by reference) for simultaneous radiation and therapeutic compound delivery treatment. In this embodiment, the use of fluid filed balloons helps to attenuate or eliminate any radioactive dose positioned within the portion of the catheter housed within the balloon. Therefore, the amount of exposed radiative wire can be regulated. The radiation emitting from the end of the wire may also be controlled using a fluid filed balloon.

Also contemplated in the present invention is that the therapeutic agent, or fluid of interest, may be delivered under pressure to the desired site as known in the art (for example, von der Leyen et al., 1999, J. Human Gene Therapy Sep. 20, 1999;10(4):2355–64; which is incorporated herein by reference).

Other variations of the present invention comprise one or more inflatable members in addition to the proximal occluding balloon and the distal occluding balloon a described in U.S. Pat. No. 4,824,436 (which is incorporated herein by reference). The one or more inflatable members may be positioned between the distal and proximal catheter occluding balloons or the one or more inflatable members may be positioned outside the region between the occluding balloons if a greater sealing effect is required between the catheter and the hollow tubular organ walls.

In another embodiment of the invention, the distal occluding balloon, the proximal occluding balloon, or both the distal and proximal occluding balloons are porous over their entire surfaces, or at specific locations on their surfaces such that therapeutic agents may be delivered to a hollow tubular organ by diffusion of a therapeutic agent through these structures (for example, Lambert et al. 1993, Coronary Artery Dis. 4: 469–475, which is incorporated herein by reference).

The local delivery device of the present invention includes a distal catheter unit adapted to slidably traverse within a proximal catheter unit. However, it is to be understood that other medical devices may be adapted to either slide within the proximal catheter unit, or slide over the distal catheter as required. Such other medical devices include catheters or wires comprising ultrasonic devices, lasers, fibre optics, or radioactive isotopes. These other devises may be used to assist in imaging the lesion site, or for treatment of the site. These other devices may be centrally disposed within the proximal catheter, thereby sliding within this catheter as needed to the treatment site, or these other devices may be disposed over the distal catheter. In either case, the other devices may interact with the distal or proximal catheter, as required, in an analogous manner (i.e. advance or retract via the adjustment mechanism) to that as described herein. A medical devise comprising a laser may be used in conjunction with the distal catheter comprising a distal catheter occluding balloon and infusion ports 110, so that flushing and cooling of the tissue being treated by laser, may take place.

The above description is not intended to limit the claimed invention in any manner, furthermore, the discussed combination of features might not be absolutely necessary for the inventive solution.

The present invention has been described with regard to preferred embodiments. However, it will be obvious to persons skilled in the art that a number of variations and modifications can be made without departing from the scope of the invention as described herein.

All references are herein incorporated by reference.

What is claimed is:

1. A local delivery device for the administration of a liquid of interest comprising:
   i) a distal catheter unit comprising a distal occluding balloon in communication with a distal occluding balloon inflation port, a distal catheter shaft comprising a plurality of infusion ports distributed within said distal catheter shaft and in fluid communication with a liquid of interest delivery port;

ii) a proximal catheter unit, comprising a proximal occluding balloon in communication with a proximal occluding balloon inflation port, and a proximal catheter shaft, said distal catheter shaft slidable within said proximal catheter shaft; and iii) an adjustment mechanism for setting a distance between said distal occluding balloon and said proximal occluding balloon.

2. The local delivery device of claim 1 wherein a valve element is associated with said adjustment mechanism, said valve element comprising an "O" ring hemostatic valve.

3. The local delivery device of claim 1, wherein said adjustment mechanism is selected from the group consisting of a threaded screw adjustment mechanism, a rack and pinion, a toothed displacement mechanism, a hydraulic regulated displacement mechanism, a compressed air regulated displacement mechanism, a frictional slide adjustment mechanism, a motor drive, and an automatic pull back, said adjustment mechanism interacting with either said distal catheter shaft, said proximal catheter shaft, or both said distal and proximal catheter shafts.

4. The local delivery device of claim 1, further comprising a quantifying device for determining said distance.

5. The local delivery device of claim 1, wherein said distal catheter unit further comprises a lumen traversing the terminal portion of said distal catheter shaft, said lumen capable of receiving a guidewire.

6. The local delivery device of claim 1, wherein said distal catheter unit further comprises a lumen traversing the entire length of said distal catheter shaft, said lumen capable of receiving a guidewire.

7. The local delivery device of claim 1, wherein said proximal catheter shaft comprises within its inner surface a sealing element, said sealing element capable of forming a seal between said proximal catheter shaft and said distal catheter shaft thereby sealing a lumen formed between said proximal and distal catheter shafts and stopping any flow of the liquid of interest past said sealing element.

8. The local delivery device of claim 1, further comprising a perfusion lumen.

9. The local delivery device of claim 1, further comprising a balloon catheter between said distal and proximal balloon catheters.

10. The local delivery device of claim 1, further comprising one or more balloon catheters outside the region between said distal and proximal balloon catheters.

11. A local delivery device comprising:

i) a distal catheter unit comprising a distal occluding balloon in communication with a distal occluding balloon inflation port, and ii) a proximal catheter unit, comprising a medical device selected from the group consisting of a laser, a fibre optic, and an ultrasound device, wherein said distal catheter shaft is slidable within said proximal catheter shaft; and iii) an adjustment mechanism for setting a distance between said distal occluding balloon and a terminal portion of said proximal catheter unit, said adjustment mechanism interacting with either said distal catheter shaft, said proximal catheter shaft, or both said distal and proximal catheter shafts, said adjustment mechanism when actuated causes said proximal catheter shaft or said distal catheter shaft to move relative to each other.

12. The local delivery device of claim 11, wherein said distal catheter shaft further comprises a plurality of infusion ports distributed within said distal catheter shaft and in fluid communication with a therapeutic agent delivery port.

13. The local delivery device of claim 11, further comprising a quantifying device for determining said distance.

14. The local delivery device of claim 11, further comprising an optical fibre.

15. The local delivery device of claim 1, further comprising a valve element associated with said adjustment mechanism, said valve element having an open position and a closed position, whereby movement of said valve element into said open position permits said adjustment mechanism to set said distance, and movement of said valve element into said closed position fixes said distance.

16. The local delivery device of claim 15, wherein the valve element comprises an "O" ring hemostatic valve.

17. The local delivery device of claim 15, wherein said adjustment mechanism is selected from the group consisting of a threaded screw adjustment mechanism, a rack and pinion, a toothed displacement mechanism, a hydraulic regulated displacement mechanism, a compressed air regulated displacement mechanism, a frictional slide adjustment mechanism, a motor drive, and an automatic pull back, said adjustment mechanism interacting with either said distal catheter shaft, said proximal catheter shaft, or both said distal and proximal shafts.

18. The local delivery device of claim 15, further comprising a quantifying device for determining said distance.

19. The local delivery device of claim 15, wherein said distal catheter unit further comprises a lumen traversing the terminal portion of said distal catheter shaft, said lumen capable of receiving a guidewire.

20. The local delivery device of claim 15, wherein said distal catheter unit further comprises a lumen traversing the entire length of said distal catheter shaft, said lumen capable of receiving a guidewire.

21. The local delivery device of claim 15, wherein said proximal catheter shaft comprises within its inner surface a sealing element, said sealing element capable of forming a seal between said proximal catheter shaft and said distal catheter shaft thereby sealing a lumen formed between said proximal and distal catheter shafts and stopping any flow of the liquid of interest past said sealing element.

22. The local delivery device of claim 15, further comprising a perfusion lumen.

23. The local delivery device of claim 15, further comprising a balloon catheter between said distal and proximal balloon catheters.

24. The local delivery device of claim 15, further comprising one or more balloon catheters outside the region between said distal and proximal balloon catheters.

25. The local delivery device of claim 11, further comprising, a valve element associated with said adjustment mechanism, said valve element having an open position and a closed position, whereby movement of said valve element into said open position permits said adjustment mechanism to set said distance, and movement of said valve element into said closed position fixes said distance.

26. The local delivery device of claim 25, wherein said distal catheter shaft further comprises a plurality of infusion ports distributed within said distal catheter shaft and in fluid communication with a therapeutic agent delivery port.

27. The local delivery device of claim 25, further comprising a quantifying device for determining said distance.

* * * * *

UNITED STATES PATENT AND TRADEMARK OFFICE
CERTIFICATE OF CORRECTION

PATENT NO. : 6,575,932 B1
DATED : June 10, 2003
INVENTOR(S) : O'Brien et al.

It is certified that error appears in the above-identified patent and that said Letters Patent is hereby corrected as shown below:

Title page,
Item [73], Assignee, delete "Ottawa Heart Institute, Ottawa (CA)" and insert
-- Ottawa Heart Institute Research Corporation, Ottawa (CA) --

Signed and Sealed this

Tenth Day of May, 2005

JON W. DUDAS
*Director of the United States Patent and Trademark Office*